United States Patent
Lee et al.

(10) Patent No.: US 9,439,628 B2
(45) Date of Patent: Sep. 13, 2016

(54) METHOD AND APPARATUS FOR CONTROLLING OUTPUT VOLTAGE OF ULTRASOUND SIGNAL

(75) Inventors: Yoon-chang Lee, Gangwon-do (KR); Tae-hyeong Oh, Gangwon-do (KR)

(73) Assignee: SAMSUNG MEDISION CO., LTD., Hongcheon-Gun, Gangwon-Do (KR)

( * ) Notice: Subject to any disclaimer, the term of this patent is extended or adjusted under 35 U.S.C. 154(b) by 554 days.

(21) Appl. No.: 13/482,430

(22) Filed: May 29, 2012

(65) Prior Publication Data
US 2013/0137978 A1 May 30, 2013

(30) Foreign Application Priority Data
Nov. 29, 2011 (KR) .................. 10-2011-0126276

(51) Int. Cl.
*A61B 8/00* (2006.01)
*G01S 7/52* (2006.01)
*A61B 8/08* (2006.01)

(52) U.S. Cl.
CPC .............. *A61B 8/54* (2013.01); *G01S 7/5202* (2013.01); *G01S 7/5205* (2013.01); *A61B 8/467* (2013.01); *A61B 8/481* (2013.01); *A61B 8/56* (2013.01)

(58) Field of Classification Search
CPC .................................................. A61B 8/54
USPC .................................... 600/437, 459
See application file for complete search history.

(56) References Cited

U.S. PATENT DOCUMENTS

| | | | |
|---|---|---|---|
| 3,732,536 A * | 5/1973 | Larka et al. | 367/135 |
| 5,151,085 A | 9/1992 | Sakurai et al. | |
| 5,482,046 A * | 1/1996 | Deitrich | G01S 7/52046 600/458 |
| 6,714,667 B1 * | 3/2004 | Mooney et al. | 382/128 |
| 2004/0249318 A1* | 12/2004 | Tanaka | 601/2 |
| 2009/0093687 A1* | 4/2009 | Telfort | A61B 5/0002 600/300 |
| 2013/0012838 A1* | 1/2013 | Jaeger et al. | 601/2 |

FOREIGN PATENT DOCUMENTS

| | | |
|---|---|---|
| JP | 63-272331 | 11/1988 |
| JP | 2006-101997 A | 4/2006 |
| JP | 2007-029191 A | 2/2007 |
| JP | 2009-142474 A | 7/2009 |
| JP | 2010-279575 A | 12/2010 |
| KR | 10-2008-0039634 A | 5/2008 |

OTHER PUBLICATIONS

Extended European Search Report issued in European Patent Application No. EP 12162586.7 dated Feb. 27, 2013.

(Continued)

*Primary Examiner* — Rochelle Turchen
(74) *Attorney, Agent, or Firm* — McDermott Will & Emery LLP (57) ABSTRACT

A method of controlling an output voltage of an ultrasound signal that is output by an ultrasound signal generating unit to a target object via a probe, the method including acquiring a target output voltage to be output by the probe to the target object and transmission conditions; acquiring property information regarding the probe; and controlling a voltage of the ultrasound signal output by the ultrasound signal generating unit based on the target output voltage, the transmission conditions, and the property information regarding the probe.

9 Claims, 6 Drawing Sheets

(56) References Cited

OTHER PUBLICATIONS

Korean Final Rejection, w/ English translation thereof, issued in Korean Patent Application No. KR 10-2011-0126276 dated May 16, 2013.

Korean Notice of Allowance, w/ English translation thereof, issued in Korean Patent Application No. KR 10-2011-0126276 dated Aug. 22, 2013.

Korean Office Action, w/ English translation thereof, issued in Korean Patent Application No. KR 10-2011-0126276 dated Dec. 20, 2012.

* cited by examiner

METHOD AND APPARATUS FOR CONTROLLING OUTPUT VOLTAGE OF ULTRASOUND SIGNAL

CROSS-REFERENCE TO RELATED PATENT APPLICATION

This application claims the benefit of Korean Patent Application No. 10-2011-0126276, filed on Nov. 29, 2011, in the Korean Intellectual Property Office, the disclosure of which is incorporated herein in its entirety by reference.

BACKGROUND OF THE INVENTION

1. Field of the Invention

The present invention relates to a method apparatus for controlling an output voltage of an ultrasound signal in such a way that a probe outputs a target output voltage in consideration of characteristics information of the probe and transmission conditions of an ultrasound system.

2. Description of the Related Art

An ultrasound diagnostic device is a device for transmitting ultrasound signals from a surface of a target object toward a predetermined region inside the target object and acquiring tomograms of soft tissues or images of blood flow based on information regarding ultrasound signals reflected by tissues inside the target object.

Advantages of such an ultrasound diagnostic device are its small size, inexpensive price, and real-time result acquisition. Furthermore, an ultrasound diagnostic device is very safe and causes no radiation exposure. Therefore, an ultrasound diagnostic device is widely used together with other types of imaging diagnostic devices, such as X-ray devices, computerized tomography (CT) scanners, magnetic resonance image (MRI) devices, scintillation cameras, etc.

Generally, outputs (transmitting voltage, pressure, and energy) of an ultrasound diagnostic device are restricted and determined based on the international standards (e.g., mechanical index (MI)). In this regard, the MI is an index that represents quantified mechanical effects of ultrasound on a human body.

Another related international standard is a thermal index (TI). Generally, the internationally permitted levels of the MI and TI are less than 1.9 and less than 6.0, respectively.

Meanwhile, an ultrasound diagnostic device is configured to output ultrasound signals having power levels that are optimized to applications without exceeding limits set by the FDA based on results of AP&I experiments. However, in some applications, e.g., a low MI environment utilizing a blood-pool contrast agent, the level of an output voltage may be changed or distorted.

SUMMARY OF THE INVENTION

According to an aspect of the present invention, there is provided a method of controlling an output voltage of an ultrasound signal that is output by an ultrasound signal generating unit to a target object via a probe, the method including acquiring a target output voltage to be output by the probe to the target object and transmission conditions; acquiring property information regarding the probe; and controlling a voltage of the ultrasound signal output by the ultrasound signal generating unit based on the target output voltage, the transmission conditions, and the property information regarding the probe.

The controlling of the voltage of the ultrasound signal output by the ultrasound signal generating unit includes detecting a first voltage with respect to an ultrasound signal input to the probe; predicting a second voltage of an ultrasound signal to be output by the probe to the target object based on the detected first voltage, the property information regarding the probe, and the transmission conditions; and in a case where a difference between the predicted second voltage and the target output voltage exceeds a predetermined tolerance, generating a new voltage level to be input to the ultrasound signal generating unit.

The generating of a new voltage level includes converting information regarding the newly generated voltage level to a predetermined bit (Binary digit) digital signal.

The method further includes, in a case where a low mechanical index (MI) mode is selected, stopping the probe from outputting ultrasound signals to the target object; and, in a case where a difference between the predicted second voltage and the target output voltage is within a predetermined tolerance, allowing the probe to output ultrasound signals to the target object.

The transmission conditions include at least one from among transmission frequency, transmission cycle, and transmission duty rate.

The controlling of the voltage of an ultrasound signal output by the ultrasound signal generating unit is repetitively performed a predetermined number of times or during a predetermined time interval.

The acquiring of the property information regarding the probe includes acquiring identification information regarding the probe; and extracting property information regarding the probe corresponding to the acquired identification information regarding the probe.

According to another aspect of the present invention, there is provided an ultrasound signal output voltage controlling apparatus including an ultrasound signal generating unit, which generates ultrasound signals; a probe, which receives ultrasound signals from the ultrasound signal generating unit and outputs the received ultrasound signals to a target object; a receiving unit, which receives a target output voltage to be output by the probe to the target object, transmission conditions, and property information regarding the probe; and a voltage control unit, which controls a voltage of an ultrasound signal output by the ultrasound signal generating unit based on the target output voltage, the transmission conditions, and the property information regarding the probe.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

In addition, although the terms used in the present invention are selected from generally known and used terms, some of the terms mentioned in the description of the present invention have been selected by the applicant at his or her discretion, the detailed meanings of which are described in relevant parts of the description herein. Furthermore, it is required that the present invention is understood, not simply by the actual terms used but by the meaning of each term lying within.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Expressions such as "at least one of," when preceding a list of elements, modify the entire list of elements and do not modify the individual elements of the list.

Hereinafter, a target object may refer to a part of a human body. For example, a target object may include an internal organ, such as a liver, heart, uterus, brain, breast, stomach, etc., or a fetus.

Hereinafter, a "user" is a medical expert, e.g., a doctor, a nurse, a medical laboratory technician, a medical imaging expert, etc., but is not limited thereto.

Hereinafter, the present invention will be described in detail by explaining preferred embodiments of the invention with reference to the attached drawings. Like reference numerals in the drawings denote like elements.

Figure 1:
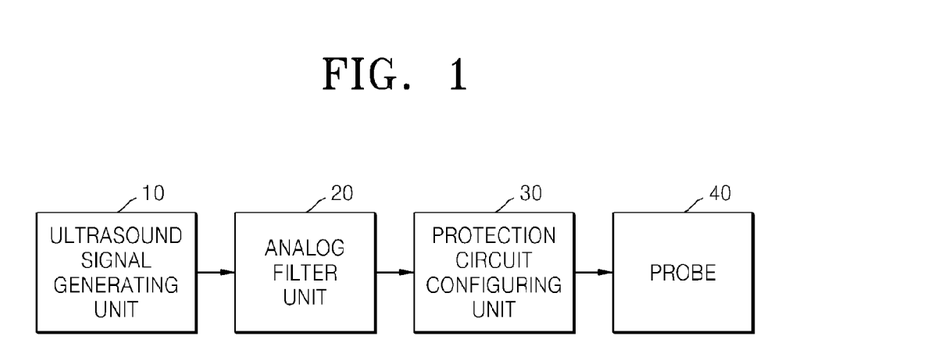
FIG. 1 is a block diagram for describing configuration of a general ultrasound diagnostic device related to an embodiment of the present invention.

FIG. 1 is a block diagram for describing configuration of a general ultrasound diagnostic device related to an embodiment of the present invention.

An ultrasound transmitting unit of a general ultrasound diagnostic device may include an ultrasound signal generating unit 10, an analog filter unit 20, a protection circuit configuring unit 30, and a probe 40.

The ultrasound signal generating unit 10 outputs ultrasound signals according to transmission conditions set by a user or system default transmission conditions of a corresponding scanning mode. Ultrasound signals output by the ultrasound signal generating unit 10 are transmitted through the analog filter unit 20 and the protection circuit configuring unit 30 and are transmitted to the probe 40.

The analog filter unit 20 functions like a low pass filter or a band pass filter to limit ultrasound signals bands and is generally formed of analog devices. Therefore, ultrasound signals output by the ultrasound signal generating unit 10, and more particularly, signals with low level voltages, are distorted.

Furthermore, the protection circuit configuring unit 30 includes a circuit for protecting an ultrasound diagnostic device, in which an ultrasound transmitting unit and a receiving unit are not separated, from being damaged when a strong transmission signal is transmitted to the receiving unit, when devices like diodes are utilized in such a circuit. However, since a diode has non-linear properties, which leads to poor performance with respect to small signals, ultrasound signals are distorted by the protection circuit configuring unit 30.

Therefore, when an ultrasound signal output by the ultrasound signal generating unit 10 passes through the analog filter unit 20 and the protection circuit configuring unit 30, the ultrasound signal is distorted, and thus a voltage of an ultrasound signal actually output by the probe 40 to a target object is lower than a voltage of an ultrasound signal output by the ultrasound signal generating unit 10.

Figure 2:
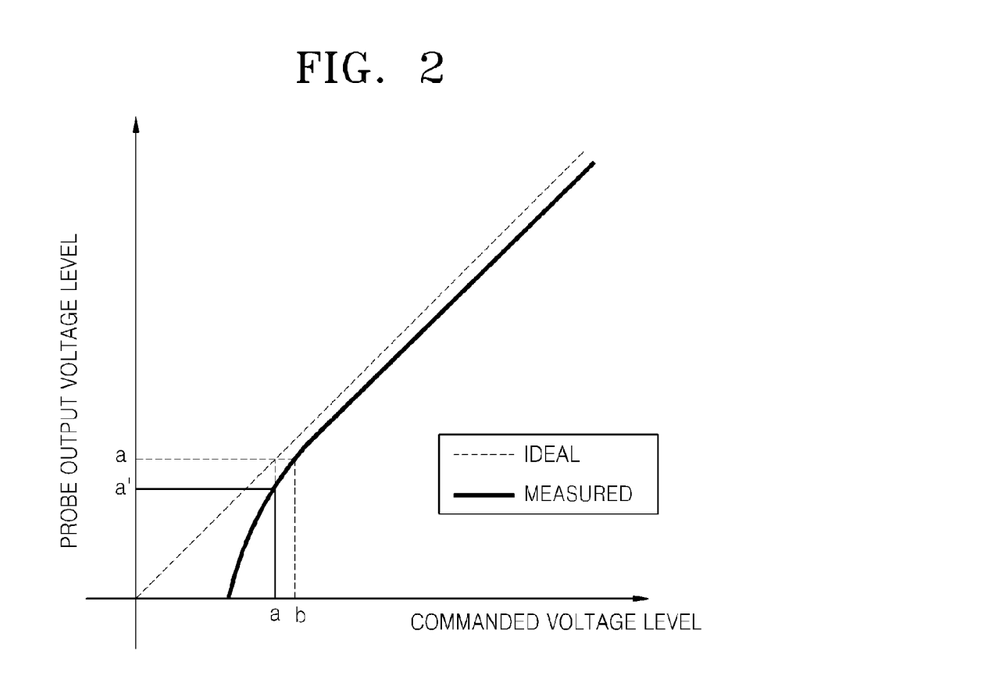
FIG. 2 is a diagram showing output voltage characteristics of a general ultrasound signal output voltage adjusting device according to an embodiment of the present invention.

For example, as shown in FIG. 2, even if a user inputs a voltage a Vpp to the ultrasound signal generating unit 10 so as to output the voltage a Vpp from the probe 40, voltage of an ultrasound signal actually output by the probe 40 becomes a' Vpp. For the probe 40 to actually output the voltage a Vpp, it is necessary to input a voltage b Vpp, which is greater than the voltage a Vpp, to the ultrasound signal generating unit 10.

An ultrasound signal output voltage adjusting device according to an embodiment of the present invention adjusts the voltage of an ultrasound signal output by the ultrasound signal generating unit 10, such that a user may adjust the voltage of an ultrasound signal output by the probe 40 to a desired output voltage. Hereinafter, configuration of an ultrasound signal output voltage adjusting device according to an embodiment of the present invention will be described in detail with reference to FIG. 3.

Figure 3:
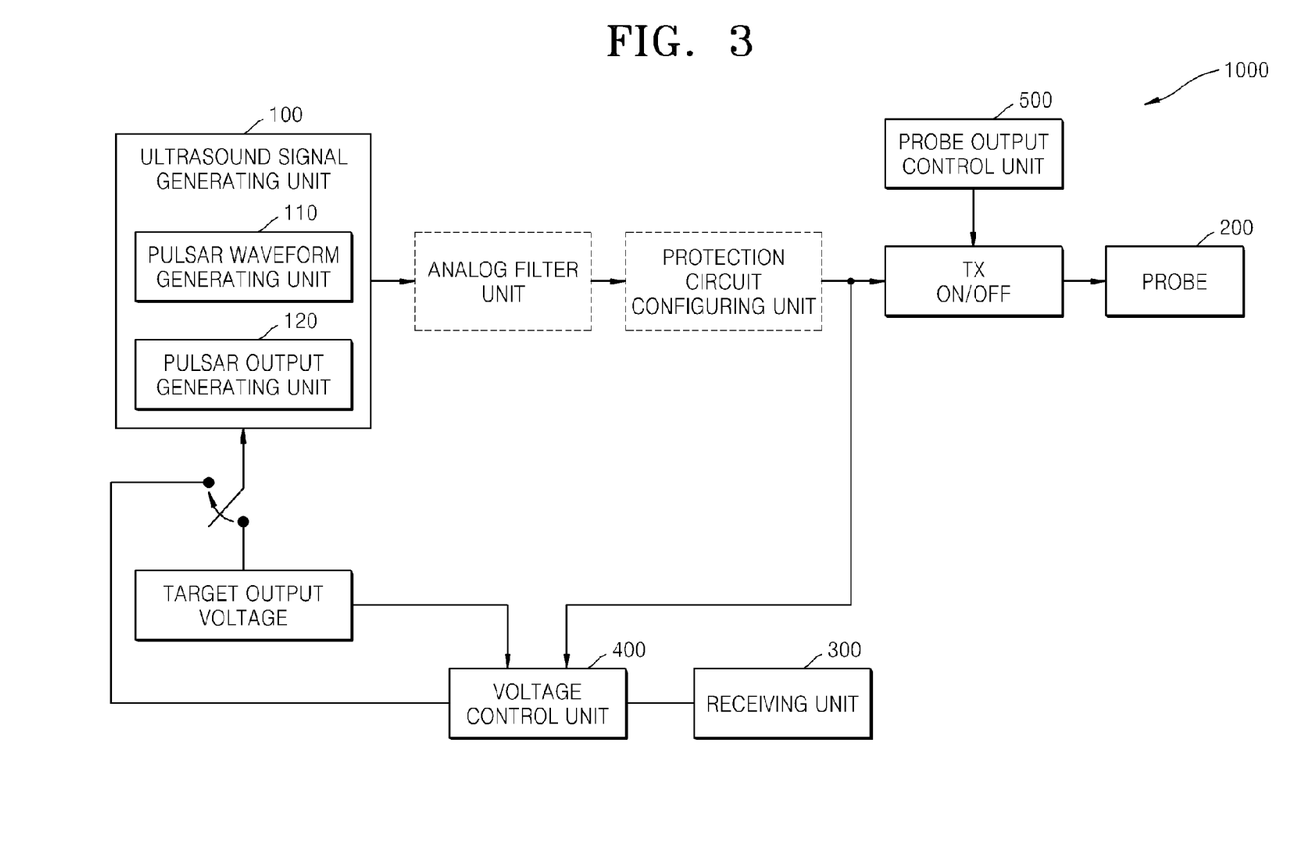
FIG. 3 is a block diagram for describing an ultrasound signal output voltage adjusting device according to an embodiment of the present invention.

FIG. 3 is a block diagram for describing an ultrasound signal output voltage adjusting device 1000 according to an embodiment of the present invention.

The ultrasound signal output voltage adjusting device 1000 according to an embodiment of the present invention is a device for controlling an output voltage of an ultrasound signal output by an ultrasound diagnostic device. The ultrasound signal output voltage adjusting device 1000 may be integrated in an ultrasound diagnostic device or may be individually embodied.

As shown in FIG. 3, according to the present embodiment, the ultrasound signal output voltage adjusting device 1000 may include an ultrasound signal generating unit 100, a probe 200, a receiving unit 300, a voltage control unit 400, a probe output control unit 500, and a memory (not shown).

However, not all of the components stated above are necessary. The ultrasound signal output voltage adjusting device 1000 may be embodied with more or less components than those stated above.

The ultrasound signal generating unit 100 may generate an ultrasound signal to be transmitted to a target object. The ultrasound signal generating unit 100 may generate an ultrasound signal based on predetermined transmission conditions.

Transmission conditions according to an embodiment of the present invention may include at least one of a transmission frequency (TX frequency), a transmission cycle (TX cycle), and a transmission pulse width ratio (TX duty rate). Furthermore, the transmission conditions according to an embodiment of the present invention may further include pulse shaping and TX apodization.

According to an embodiment of the present invention, a target output voltage may be input to the ultrasound signal generating unit 100. The term 'target output voltage' refers to a voltage a user desires to output to a target object via the probe 200. In other words, according to an embodiment of the present invention, a user or the ultrasound signal output voltage adjusting device 1000 may determine a target output voltage and may input the target output voltage to the ultrasound signal generating unit 100.

Furthermore, according to an embodiment of the present invention, the voltage control unit 400 may input a new voltage level to the ultrasound signal generating unit 100. In this case, the ultrasound signal generating unit 100 may generate an ultrasound signal based on the new voltage level.

According to an embodiment of the present invention, the ultrasound signal generating unit 100 may include a pulsar waveform generating unit 110 and a pulsar output generating unit 120.

The pulsar waveform generating unit 110 may generate an ultrasound output waveform based on at least one of the TX frequency, TX cycle, and TX duty rate. Shapes of an ultrasound output waveform according to an embodiment of the present invention may vary. The pulsar output generating unit 120 may generate an ultrasound signal by applying a predetermined power level to the ultrasound output waveform generated by the pulsar waveform generating unit 110.

Figure 4:
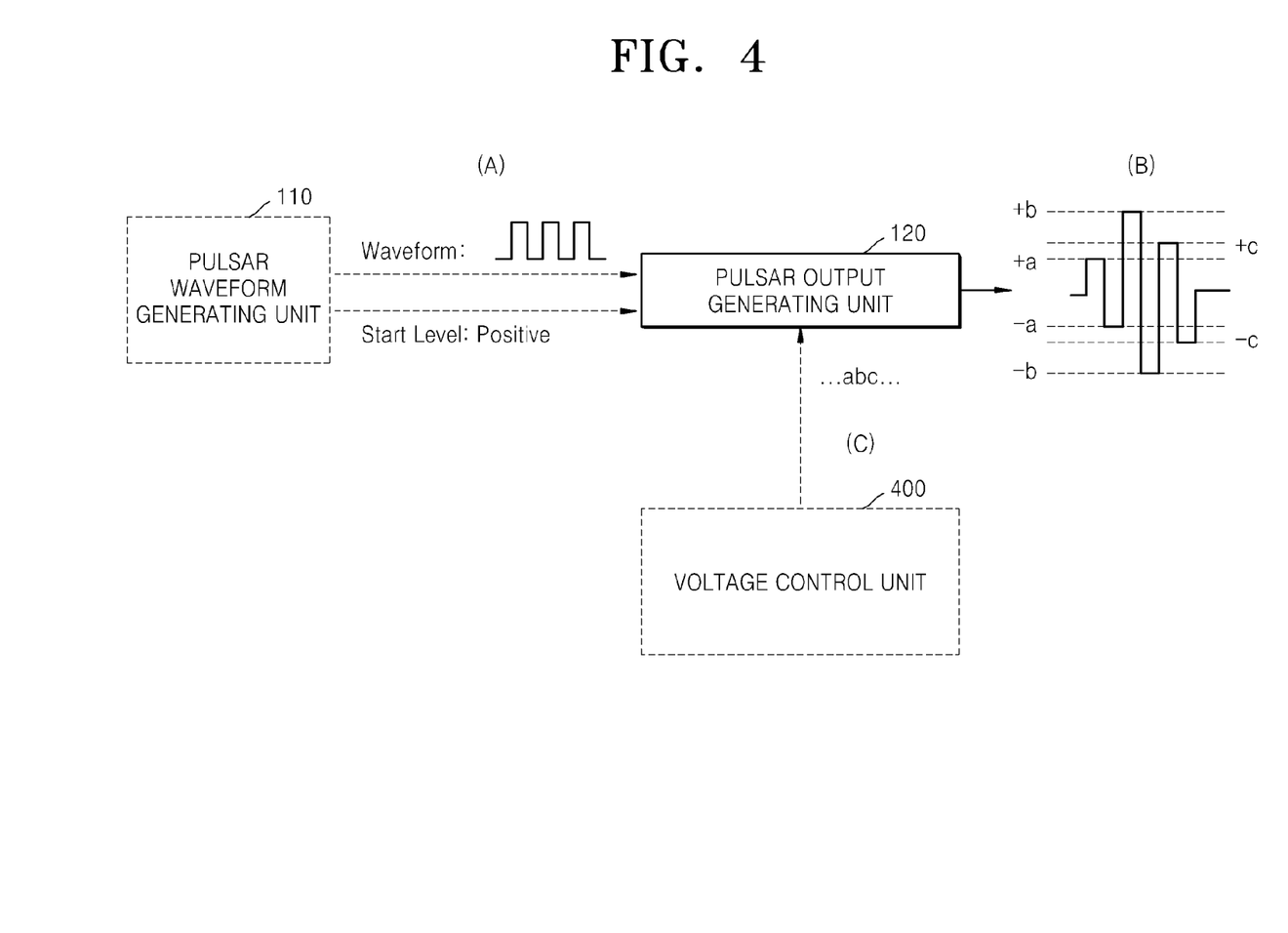
FIG. 4 is a diagram for describing an ultrasound signal generating unit according to an embodiment of the present invention.

For example, as shown in FIG. 4, the pulsar waveform generating unit 110 may generate a rectangular ultrasound output waveform A. In this case, the pulsar output generating unit 120 generates an ultrasound signal B based on the ultrasound output waveform A received from the pulsar waveform generating unit 110 and a voltage level C received from the voltage control unit 400.

Referring back to FIG. 3, the probe 200 may receive an ultrasound signal output by the ultrasound signal generating unit 100 and output the received ultrasound signal to a target object. Furthermore, the probe 200 may receive an ultrasound echo signal corresponding to the output ultrasound signal. According to an embodiment of the present invention, frequency response characteristics of the probe 200 may vary according to manufacturers of the probe 200.

The probe 200 according to an embodiment of the present invention may include at least one of a 1-dimensional (1D) probe, a 1.5D probe, and a 2D (matrix) probe.

The receiving unit 300 may acquire a target output voltage to be output by the probe 200 to the target object. According to an embodiment of the present invention, a user may input a target output voltage via a user input unit (not shown).

A user input unit according to an embodiment of the present invention may include a keypad, a dome switch, a touchpad (resistive/capacitive), a jog wheel, a jog switch, etc. Particularly, if a touchpad and a display unit constitute a layered structure, the layered structure may be referred to as a touch screen.

The receiving unit 300 may acquire transmission conditions. In other words, the receiving unit 300 may acquire at least one of the TX frequency, TX cycle, and TX duty rate.

Furthermore, according to an embodiment of the present invention, the receiving unit 300 may receive mode selecting information. In this case, transmission conditions may be changed according to the mode selecting information. For example, if a user selects at least one of a Pen mode, a Gen mode, and a Res mode, transmission conditions may be changed to the TX frequency, TX cycle, and TX duty rate that correspond to the selected mode(s).

According to an embodiment of the present invention, the receiving unit 300 may acquire property information regarding the probe 200. The property information regarding the probe 200 according to an embodiment of the present invention may refer to information regarding frequency response characteristics of the probe 200. For example, property information regarding the probe 200 may include gain values of the probe 200 according to frequencies.

The voltage control unit 400 may control voltage of an ultrasound signal output by the ultrasound signal generating unit 100 based on the predetermined transmission information and the property information regarding the probe 200. For example, the voltage control unit 400 may control voltage of an ultrasound signal output by the ultrasound signal generating unit 100 in a case where a difference between a predicted voltage of an ultrasound signal expected to be output by the probe 200 and a target output voltage exceeds a predetermined tolerance.

According to an embodiment of the present invention, the voltage control unit 400 may control voltages of ultrasound signals output by the ultrasound signal generating unit 100 a predetermined number of times or during a predetermined time interval.

According to another embodiment of the present invention, the voltage control unit 400 may control a voltage of an ultrasound signal output by the ultrasound signal generating unit 100 when a mode is changed. For example, if a blood-pool contrast agent mode is selected, the voltage control unit 400 may adjust a voltage of an ultrasound signal output by the ultrasound signal generating unit 100.

In a low MI environment utilizing an ultrasound blood-pool contrast agent, an ultrasound signal output by the ultrasound signal generating unit 100 may be significantly distorted, and thus a voltage actually output by the probe 200 may be significantly lower than a target output voltage.

A detailed description of the voltage control unit 400 will be given below with reference to FIG. 5.

In a case where a low MI mode is selected, the probe output control unit 500 may stop the probe 200 from outputting ultrasound signals to a target object. Since a difference between a target output voltage and a voltage actually output by the probe 200 increases in a low MI mode, it is necessary to compensate a voltage of an ultrasound signal, such that the voltage output by the probe 200 is close to the target output voltage.

In a case where a difference between a predicted voltage of an ultrasound signal expected to be output by the probe 200 and a target output voltage is within a predetermined tolerance, the probe output control unit 500 may allow the probe 200 to output ultrasound signals to a target object. In this case, the probe 200 may output an ultrasound signal with a voltage within a tolerance of a target output voltage to the target object.

A memory (not shown) may store a program for controlling the voltage control unit 400 and may temporarily store data that is input/output. For example, the memory (not shown) may store a probe property table. The probe property table may include probe identification information and frequency response characteristics corresponding to the probe identification information. Furthermore, the memory (not shown) may store transmission conditions respectively corresponding to modes.

The memory (not shown) may include at least one from among a flash memory type storage device, a hard disk type storage device, a multimedia card micro type storage device, a card type memory device (e.g., a SD memory or a XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disc. Furthermore, the ultrasound signal output voltage adjusting device 1000 may operate web storage which functions as a storage device on the internet.

Figure 5:
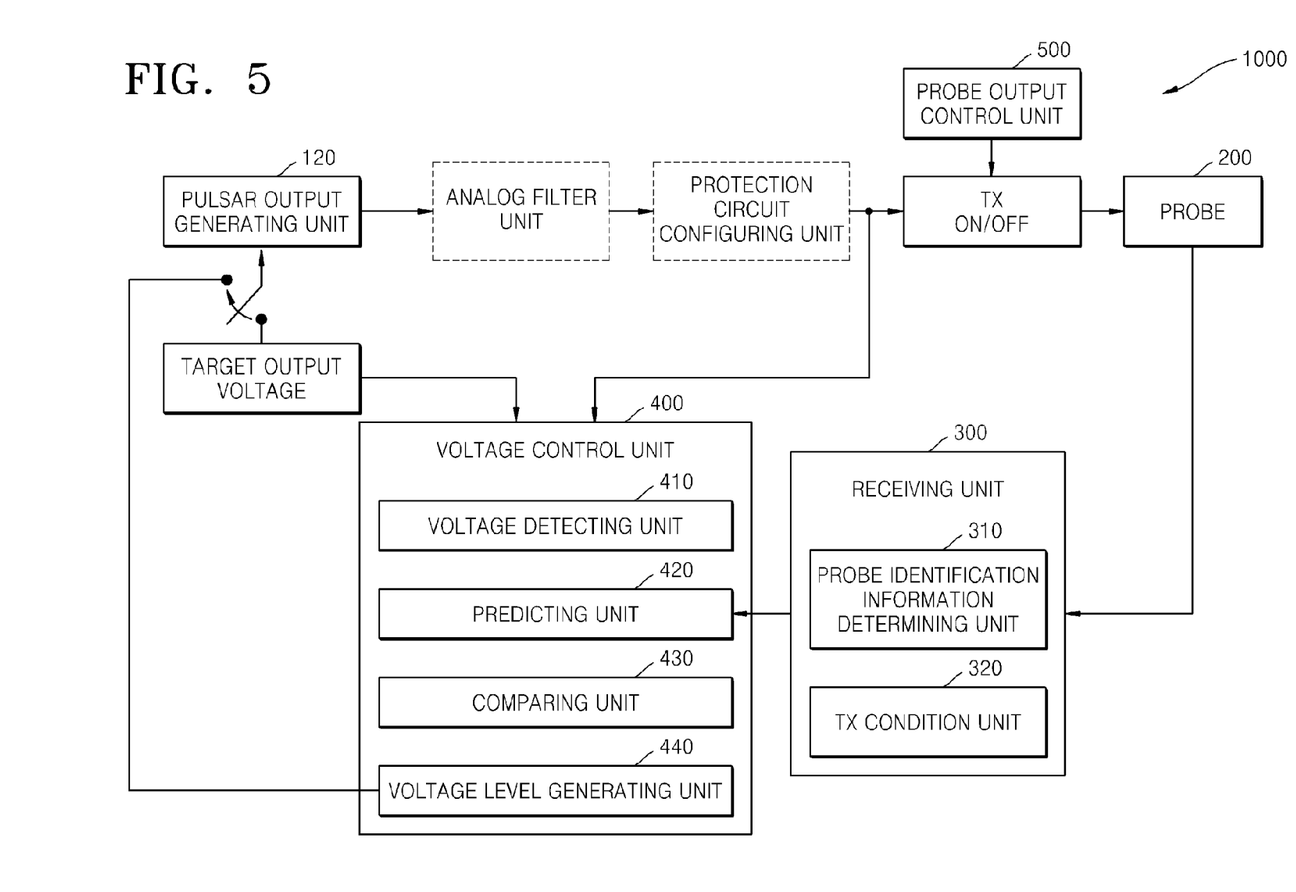
FIG. 5 is a diagram for describing a voltage control unit according to an embodiment of the present invention.

FIG. 5 is a diagram for describing the voltage control unit 400 according to an embodiment of the present invention.

As shown in FIG. 5, the voltage control unit 400 according to an embodiment of the present invention may include a voltage detecting unit 410, a predicting unit 420, a comparing unit 430, and a voltage level generating unit 440. However, not all of the components stated above are necessary. The voltage control unit 400 may be embodied with more components than the components stated above or less components than the components stated above.

The voltage detecting unit 410 may detect a first voltage with respect to an ultrasound signal input to the probe 200. According to an embodiment of the present invention, since an ultrasound signal output by the ultrasound signal generating unit 100 is distorted as the ultrasound signal passes through an analog filter unit and a protection circuit configuring unit, voltage of an ultrasound signal input to the probe 200 may be lower than voltage of the ultrasound signal output by the ultrasound signal generating unit 100.

The predicting unit 420 may predict a second voltage to be output by the probe 200 to a target object. In this case, the predicting unit 420 may predict the second voltage based on property information regarding the probe 200 and transmission conditions that are acquired by the receiving unit 300 based on the first voltage.

According to an embodiment of the present invention, the receiving unit 300 may include a probe identification information determining unit 310. The probe identification information determining unit 310 may acquire identification information regarding a probe and extract property information regarding the probe in correspondence to the acquired identification information. Identification information regarding a probe may include an ID, a product code, and model information regarding the probe.

According to an embodiment of the present invention, the receiving unit 300 may further include a TX condition unit 320. The TX condition unit 320 may extract predetermined transmission conditions. For example, the TX condition unit 320 may extract transmission conditions corresponding to a mode selected by a user.

The comparing unit 430 compares the predicted second voltage to the target output voltage and determines whether a difference between the second voltage and the target output voltage is within a predetermined tolerance.

In a case where the difference between the predicted second voltage and the target output voltage exceeds the predetermined tolerance, the voltage level generating unit 440 may generate a new voltage level to be input to the ultrasound signal generating unit 100.

Furthermore, the voltage level generating unit 440 may convert information regarding the new voltage level to a predetermined bit (Binary digit) digital signal. For example, in a case where power is controlled with 8 bits digital signal, the voltage level generating unit 440 may indicate 0 Vpp as '00000000' and may indicate 200 Vpp or the maximum voltage as '11111111.'

Figure 6:
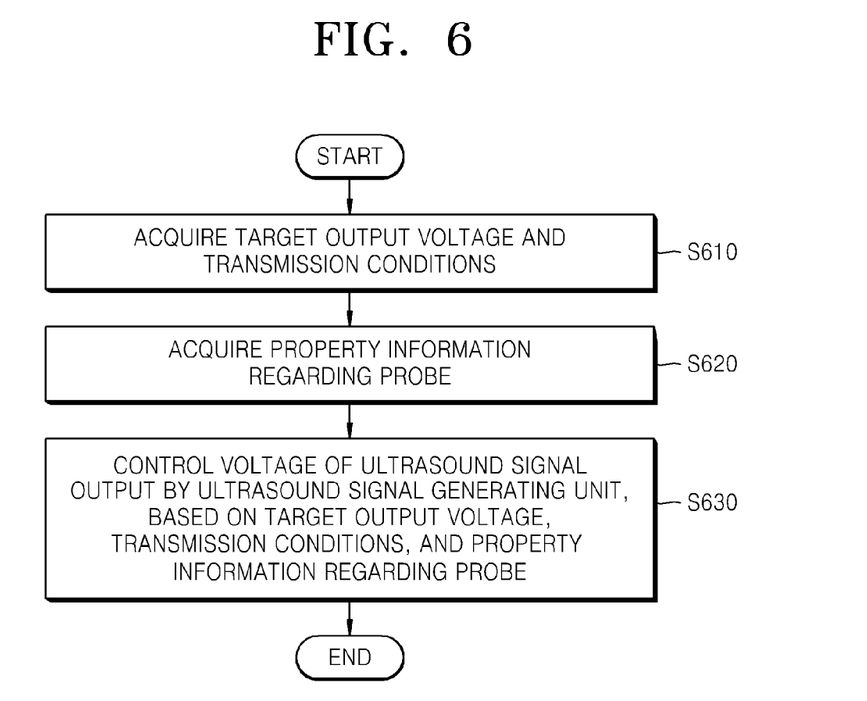
FIG. 6 is a flowchart for describing a method of controlling an output voltage of an ultrasound signal according to an embodiment of the present invention.

FIG. 6 is a flowchart for describing a method of controlling an output voltage of an ultrasound signal according to an embodiment of the present invention.

Referring to FIG. 6, the method of controlling output voltage of an ultrasound signal includes operations that are chronologically performed by the ultrasound signal output voltage adjusting device 1000 shown in FIGS. 3 and 5. Therefore, even if omitted below, any descriptions given above regarding the ultrasound signal output voltage adjusting device 1000 shown in FIGS. 3 and 5 may also be applied to the method of controlling output voltage of an ultrasound signal shown in FIG. 6.

As shown in FIG. 6, according to an embodiment of the present invention, the ultrasound signal output voltage adjusting device 1000 may acquire a target voltage to be output by the probe 200 to a target object and transmission conditions (operation S610).

For example, the ultrasound signal output voltage adjusting device 1000 may receive an input of 100 Vpp from a user as a target output voltage. Furthermore, the ultrasound signal output voltage adjusting device 1000 may extract predetermined transmission conditions (e.g., TX frequency, TX cycle, TX duty rate, etc.) corresponding to a mode selected by the user.

According to an embodiment of the present invention, the ultrasound signal output voltage adjusting device 1000 may acquire property information regarding the probe 200 (operation S620). For example, the receiving unit 300 may receive identification information of the probe 200 connected to the ultrasound signal output voltage adjusting device 1000 and may extract property information of the probe 200 corresponding to the received identification information from a memory.

If a plurality of probes 200 are connected to the ultrasound signal output voltage adjusting device 1000, the receiving unit 300 may receive identification information regarding the probe 200 selected by a user from among the plurality of probes 200. In this case, the receiving unit 300 extracts property information regarding the probe 200 corresponding to the identification information of the selected probe 200.

According to an embodiment of the present invention the ultrasound signal output voltage adjusting device 1000 may control voltage of an ultrasound signal output by the ultrasound signal generating unit 100, based on the target output voltage, the transmission conditions, and the property information regarding the probe 200 (operation S630).

Figure 7:
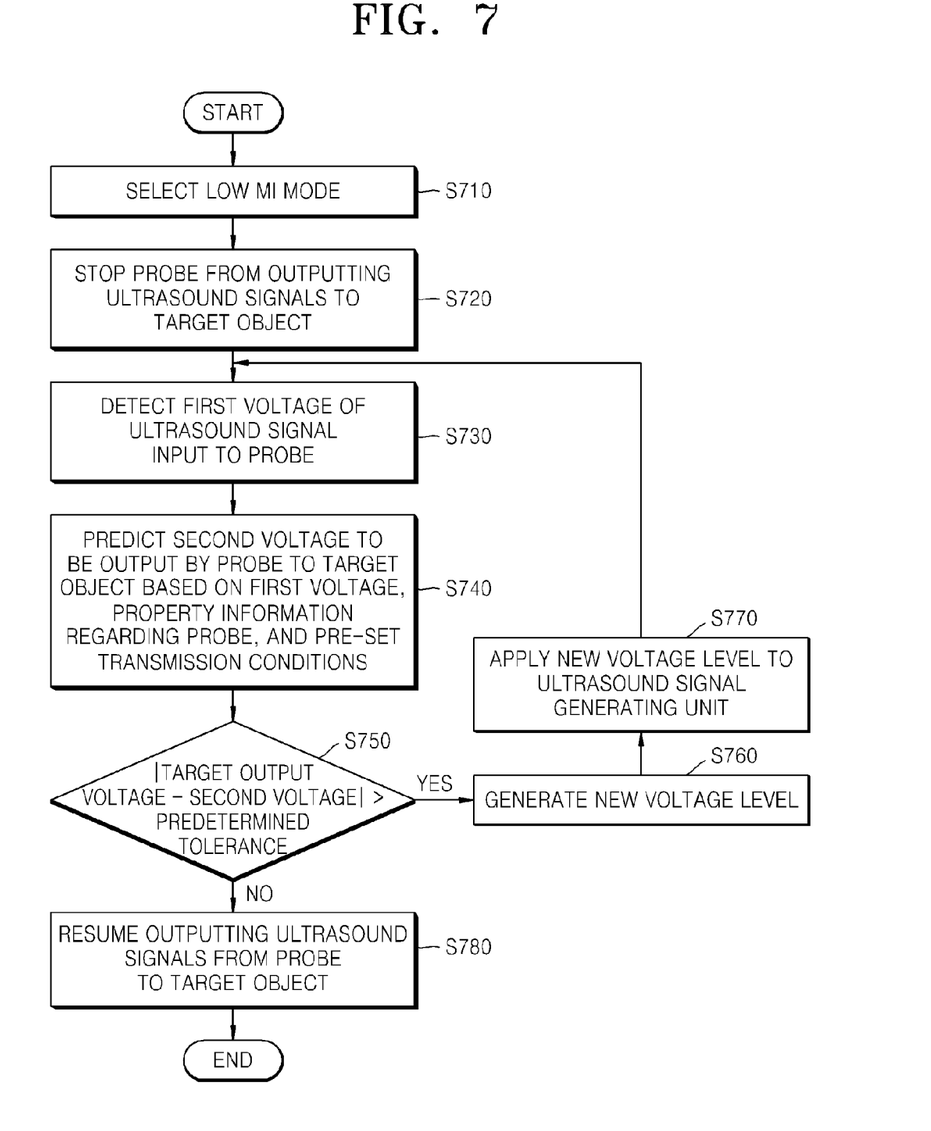
FIG. 7 is a flowchart for describing in detail a method of controlling an output voltage of an ultrasound signal according to the present embodiment.

FIG. 7 is a flowchart for describing in detail a method of controlling an output voltage of an ultrasound signal according to the present embodiment.

Referring to FIG. 7, the method of controlling output voltage of an ultrasound signal includes operations that are chronologically performed by the ultrasound signal output voltage adjusting device 1000 shown in FIGS. 3 and 5. Therefore, even if omitted below, any descriptions given above regarding the ultrasound signal output voltage adjusting device 1000 shown in FIGS. 3 and 5 may also be applied to the method of controlling an output voltage of an ultrasound signal shown in FIG. 7.

According to an embodiment of the present invention, the ultrasound signal output voltage adjusting device 1000 may receive an external selection of a low MI mode (operation S710). The low MI mode refers to a mode requiring an acoustic pressure significantly lower than that of common ultrasound imaging generating condition. For example, in a case of acquiring an ultrasound image by using a contrast agent, a low MI mode may be used to prevent the contrast agent from being burst and to maintain nonlinear resonance characteristics.

A contrast agent refers to a chemical that is injected into blood vessels for acquiring clear views of tissues or blood vessels. For example, contrast agents according to an embodiment of the present invention may include ultrasound contrast agents, micro-bubbles, etc. A size of a contrast agent according to an embodiment of the present invention may be smaller than or equal to that of a red blood cell.

Resonance characteristics of contrast agents may vary according to manufacturers or products. For example, a contrast agent manufactured by a company A may exhibit linear resonance characteristics at a acoustic pressure around 50 kPa, may exhibit nonlinear resonance characteristics at a acoustic pressure around 100 kPa, and may burst at an acoustic pressure equal to or higher than 150 kPa. Meanwhile, a contrast agent manufactured by a company B may burst at an acoustic pressure equal to or higher than 130 kPa.

In a case where a low MI mode is selected, the ultrasound signal output voltage adjusting device 1000 may stop the probe 200 from outputting ultrasound signals to a target object (operation S720). The reason is that, since ultrasound signals may be distorted more significantly in a low MI mode, it is necessary to compensate voltage of ultrasound signals output by the probe 200.

The ultrasound signal output voltage adjusting device 1000 may detect a first voltage of an ultrasound signal input to the probe 200 (operation S730). The ultrasound signal output voltage adjusting device 1000 may predict a second voltage to be output by the probe 200 to a target object based on the first voltage, property information regarding the probe 200, and predetermined transmission conditions (operation S740).

According to an embodiment of the present invention, since property information regarding the probe 200 includes frequency response values of probes, the ultrasound signal output voltage adjusting device 1000 receives identification information regarding the probe 200 that is either currently connected or is selected by a user and extracts a frequency response curve of the probe 200 corresponding to the received identification information.

In this case, the ultrasound signal output voltage adjusting device 1000 may apply a TX frequency from among the predetermined transmission conditions to the extracted frequency response curve of the probe 200 and acquire a gain value of the probe 200 according to the TX frequency.

The ultrasound signal output voltage adjusting device 1000 predicts a second voltage with respect to an ultrasound signal to be output by the probe 200 to a target object by applying the gain value of the probe 200 to the detected first voltage.

According to an embodiment of the present invention, the ultrasound signal output voltage adjusting device 1000 determines whether a difference between the second voltage and the target output voltage is within a predetermined tolerance (operation S750).

In a case where the difference between the predicted second voltage and the target output voltage exceeds the predetermined tolerance, the ultrasound signal output voltage adjusting device 1000 generates a new voltage level to be input to the ultrasound signal generating unit 100 (operation S760).

At this point, the ultrasound signal output voltage adjusting device 1000 applies the newly generated voltage level to the ultrasound signal generating unit 100 (operation S770). According to an embodiment of the present invention, the ultrasound signal output voltage adjusting device 1000 may convert information regarding the new voltage level to a predetermined bit digital signal and apply the digital signal to the ultrasound signal generating unit 100.

In a case where the difference between the predicted second voltage and the target output voltage is within the predetermined tolerance, the ultrasound signal output voltage adjusting device 1000 may allow the probe 200 to output ultrasound signals to a target object.

For example, it is assumed below that a user sets a target output voltage to 100 Vpp and sets a tolerance to 1 Vpp. If the user applies the target output voltage or 100 Vpp to the ultrasound signal generating unit 100, a second voltage of an ultrasound signal expected to be output by the probe 200 may be 90 Vpp. In this case, since a difference between the target output voltage (=100 Vpp) and the second voltage (=90 Vpp) is 10 Vpp, the difference (=10 Vpp) exceeds the tolerance (=1 Vpp), and thus the ultrasound signal output voltage adjusting device 1000 may generate a new voltage level of 120 Vpp.

In a case where the ultrasound signal output voltage adjusting device 1000 applies the new voltage level of 120 Vpp to the ultrasound signal generating unit 100, a second voltage of an ultrasound signal expected to be output by the probe 200 may be 107 Vpp. In this case, since a difference between the target output voltage (=100 Vpp) and the second voltage (=107 Vpp) is 7 Vpp, the difference (=7 Vpp) exceeds the tolerance (=1 Vpp), and thus the ultrasound signal output voltage adjusting device 1000 may generate a new voltage level of 110 Vpp.

In a case where the ultrasound signal output voltage adjusting device 1000 applies the new voltage level of 110 Vpp to the ultrasound signal generating unit 100, a second voltage of an ultrasound signal expected to be output by the probe 200 may be 99.5 Vpp. In this case, since a difference between the target output voltage (=100 Vpp) and the second voltage (=99.5 Vpp) is 0.5 Vpp, the difference (=0.5 Vpp) is smaller than the tolerance (=1 Vpp), and thus the ultrasound signal output voltage adjusting device 1000 does not generate a new voltage level and allows the probe 200 to output ultrasound signals to a target object. Therefore, the probe 200 may output an ultrasound signal with a voltage of 99.5 Vpp.

According to an embodiment of the present invention, an ultrasound diagnostic device may stably output ultrasound signals whose output voltage is close to a target output voltage via a probe. Furthermore, according to an embodiment of the present invention, an ultrasound diagnostic device may automatically adjust a transmitting voltage to a target voltage level even if transmission conditions change.

Furthermore, according to an embodiment of the present invention, in a low MI mode using an ultrasound contrast agent or micro-bubbles, an ultrasound diagnostic device may change acoustic pressures for maximizing sensitivity of an ultrasound image without bursting the micro-bubbles.

A method according to an embodiment of the present invention may be embodied in the form of program commands that may be carried out by various computer devices and may be stored in a computer readable recording medium. The computer readable recording medium may include program commands, data files, data structures, or combinations thereof. The program commands stored in the computer readable recording medium may be either exclusively designed and configured for the present invention or known in the art. Examples of computer readable recording media include magnetic media, such as a floppy disk and a magnetic tape, optical media, such as a CD-ROM and a DVD, magneto-optical media, such as a floptical disk, and hardware devices exclusively configured to store and carry out program commands, such as a ROM, a RAM, and a flash memory. Examples of the program commands include not only machine languages generated by compliers, but also high-level languages that may be carried out by a computer via an interpreter.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of controlling an output voltage of an ultrasound signal that is output by a probe to a target object, the method comprising:
   acquiring property information regarding the probe, the property information defining a relationship between frequency information and gain information;
   detecting a first voltage of the ultrasound signal which is input to the probe;
   determining a gain value according to a transmission frequency of the ultrasound signal and the property information of the probe;
   predicting a second voltage of the ultrasound signal to be output by the probe to the target object according to the detected first voltage and the gain value; and
   in a case where a difference between the predicted second voltage of the ultrasound signal to be output by the probe to the target object and a target output voltage to be output to the target object exceeds a predetermined tolerance, generating a new voltage level to be input to an ultrasound signal generator for driving the probe.

2. The method of claim 1, wherein the generating a new voltage level comprises converting information regarding the newly generated voltage level to a predetermined bit (Binary digit) digital signal.

3. The method of claim 1, further comprising:
   receiving a selection of a low mechanical index (MI) mode;
   stopping the probe from outputting ultrasound signals to the target object according to the selection; and
   in a case where a difference between the predicted second voltage and the target output voltage is within a predetermined tolerance, allowing the probe to output ultrasound signals to the target object.

4. The method of claim 1, wherein the acquiring property information regarding the probe comprises:
   acquiring identification information regarding the probe; and
   extracting property information regarding the probe corresponding to the acquired identification information regarding the probe.

5. An ultrasound signal output voltage controlling apparatus comprising:
   an ultrasound signal generator configured to generate ultrasound signals;
   a probe configured to receive ultrasound signals from the ultrasound signal generator and output the received ultrasound signals to a target object;
   a receiver configured to receive property information regarding the probe, the property information defining a relationship between frequency information and gain information;
   a voltage detector configured to detect a first voltage of an ultrasound signal which is input to the probe;
   a voltage controller configured to determine a gain value according to a transmission frequency of the ultrasound signal and the property information of the probe, and to predict a second voltage of the ultrasound signal to be output by the probe to the target object according to the detected first voltage and the gain value; and
   a voltage level generator configured to generate a new voltage level to be input to the ultrasound signal generator for driving the probe, in a case where a difference between the predicted second voltage of the ultrasound signal to be output by the probe to the target object and a target output voltage to be output to the target object exceeds a predetermined tolerance.

6. The ultrasound signal output voltage controlling apparatus of claim 5, wherein the voltage level generator converts information regarding the newly generated voltage level to a predetermined bit(Binary digit) digital signal.

7. The ultrasound signal output voltage controlling apparatus of claim 5, wherein the receiver is configured to receive a selection of a low mechanical index (MI) mode, and
   further comprising a probe output controller configured to stop the probe from outputting ultrasound signals to the target object according to the selection of the low mechanical index (MI) mode and allow the probe to output ultrasound signals to the target object in a case where a difference between the predicted second voltage and the target output voltage is within a predetermined tolerance.

8. The ultrasound signal output voltage controlling apparatus of claim 5, wherein the receiver acquires identification information regarding the probe and extracts property information regarding the probe corresponding to the acquired identification information regarding the probe.

9. A non-transitory computer readable recording medium having recorded thereon a computer program for implementing the method of controlling an output voltage of an ultrasound signal that is output by a probe to a target object, the method comprising:
   acquiring a target output voltage to be output by the probe to the target object and transmission conditions;
   acquiring property information regarding the probe, the property information defining a relationship between frequency information and gain information;
   detecting a first voltage of the ultrasound signal which is input to the probe;
   determining a gain value according to a transmission frequency of the ultrasound signal and the property information of the probe;
   predicting a second voltage of the ultrasound signal to be output by the probe to the target object according to the detected first voltage and the gain value; and
   in a case where a difference between the predicted second voltage of the ultrasound signal to be output by the probe to the target object and a target output voltage to be output to the target object exceeds a predetermined tolerance, generating a new voltage level to be input to an ultrasound signal generator for driving the probe.

* * * * *

UNITED STATES PATENT AND TRADEMARK OFFICE
CERTIFICATE OF CORRECTION

PATENT NO. : 9,439,628 B2  
APPLICATION NO. : 13/482430  
DATED : September 13, 2016  
INVENTOR(S) : Yoon-Chang Lee et al.

Page 1 of 1

It is certified that error appears in the above-identified patent and that said Letters Patent is hereby corrected as shown below:

On the Title Page

Item (73) Assignee should read:  
(73) Assignee: SAMSUNG MEDISON CO., LTD., Hongcheon-Gun, Gangwon-Do (KR)

Signed and Sealed this  
Fifteenth Day of August, 2017

Joseph Matal  
*Performing the Functions and Duties of the*  
*Under Secretary of Commerce for Intellectual Property and*  
*Director of the United States Patent and Trademark Office*